United States Patent
Van Der Puy

(10) Patent No.: US 6,265,616 B1
(45) Date of Patent: Jul. 24, 2001

(54) MANUFACTURE OF TRIFLUORISOPROPYLAMINE

(75) Inventor: Michael Van Der Puy, Amherst, NY (US)

(73) Assignee: Honeywell International Inc., Morris Township, NJ (US)

( * ) Notice: Subject to any disclaimer, the term of this patent is extended or adjusted under 35 U.S.C. 154(b) by 0 days.

(21) Appl. No.: 09/493,162

(22) Filed: Jan. 27, 2000

Related U.S. Application Data

(60) Provisional application No. 60/118,993, filed on Feb. 8, 1999.

(51) Int. Cl.$^7$ .................................................. C07C 209/40
(52) U.S. Cl. .............................................. 564/489
(58) Field of Search .............................................. 564/489

(56) References Cited

U.S. PATENT DOCUMENTS

| | | | |
|---|---|---|---|
| 4,378,366 | * 3/1983 | Malen et al. | 424/272 |
| 5,922,917 | * 7/1999 | Nardi et al. | 564/489 |

OTHER PUBLICATIONS

Albert L. Henne et al., "Acidity of Trifluorinated Alcohols and Saponification Rates of their Acetates.", Mar. 20, 1952, vol. 74, pp. 1426–1428.

J.B. Dickey et al., "Fluorinated Aminoanthraquinone Dyes.", Feb. 1956, *Industrial and Engineering Chemistry*, vol. 48, No. 2, pp. 209–213.

Maynard S. Raasch, "The Chemistry of Sulfur Tetrafluoride. IX. Reaction with Amino Acids in Hydrogen Fluoride.", Apr. 1962, vol. 27, pp. 1406–1409.

Robert A. Shepard, et al., "1,1,1–Trifluoro–2–diazopropane.", Oct. 8, 1965, vol. 31, p. 964.

Taizo Ono, et al., "Biomimetic Reductive Amination of Fluoro Aldehydes and Ketones via [1,3]–Proton Shift Reaction. Scope and Limitations.", Mar. 1996, vol. 61, pp. 6563–6569.

Vadim A. Soloshonok, et al., "Highly Enantioselective Transfer of Chirality from a Less to a More Configurationally Unstable Sterogenic Center. A Practical Asymmetric Synthesis of (Fluoroalkyl)amines via Biomimetic Transamination.", Mar. 1997, vol. 62, pp. 3030–3031 and supplementary material.

* cited by examiner

*Primary Examiner*—Johann Richter
*Assistant Examiner*—Brian J. Davis
(74) *Attorney, Agent, or Firm*—Colleen D. Szuch

(57) ABSTRACT

The invention provides a process for preparing trifluoroisopropylamine. Trifluoroisopropylamine is produced by reducing trifluoroacetone oxime with hydrogen, in the vapor phase, in the presence of a reduction catalyst. Trifluoroisopropylamine is useful intermediate in the preparation of fluorinated pharmaceutical compounds such as antihypertensives.

22 Claims, No Drawings

MANUFACTURE OF TRIFLUORISOPROPYLAMINE

CROSS REFERENCE TO RELATED APPLICATION

This application claims the benefit of U.S. provisional patent application Ser. No. 60/118,993 filed Feb. 8, 1999, which is incorporated herein by reference.

BACKGROUND OF THE INVENTION

The present invention relates to partially fluorinated amines, or more particularly to a process for preparing trifluoroisopropylamine.

Partially fluorinated amines are known in the art to be useful chemical intermediates. In particular, 1,1,1-trifluoro-2-propylamine, or trifluoroisopropylamine, is known to be a useful intermediate in the preparation of fluorinated pharmaceutical compounds such as antihypertensives. Such use is described in U.S. Pat. No. 4,378,366, which is incorporated herein by reference. Trifluoroisopropylamine has also been used in the manufacture of dyes. (See, J. B. Dickey et al., Ind. Eng. Chem., 48 (1956) 209).

Trifluoroisopropylamine ($CF_3CH(CH_3)NH_2$) has been made by several routes, however none are of these methods are favorable for large scale manufacture. One process involves a reaction of alanine with sulfur tetrafluoride. However, the desired amine is only produced in 29% yield, and the process uses an expensive and toxic raw material, $SF_4$, under pressure in a batch process. (See M. S. Raash, J. Org. Chem., 27 (1962) 1406). In another process, a hydrochloride salt is produced rather than producing the amine directly. This salt is prepared from the hydrolysis of the N-benzylidene derivative of trifluoroisopropylamine, which in turn was prepared in two steps from 1,1,1,5,5,5-hexafluoro-2,4-pentanedione. The initial reaction from this expensive starting material gives the desired intermediate, N-benzylimine of trifluoroacetone, but in only 29% yield. (See T. Ono, et al, J. Org. Chem., 61 (1966) 6563). In an improved variation of this procedure, trifluoroacetone is treated with phenylethylamine in ether in the presence of molecular sieves to give the corresponding imine. (See V. A. Soloshonok, et al, J. Org. Chem., 62 (1997) 3030). This is followed by isomerization with a base and, finally, hydrolysis to give trifluoroisopropylamine hydrochloride. While the overall yield of the salt is good, the process involves the use of an expensive base and its separation from the isomerization product.

One attractive method for commercial-scale manufacture of trifluoroisopropylamine is a 3-step process starting with the preparation of trifluoroacetone in 83% yield from the commercially available ethyl trifluoroacetoacetate. (See A. L. Henne and R. L. Pelley, J. Am. Chem. Soc., 74 (1952) 1426). The trifluoroacetone is then converted into its corresponding oxime in 85% yield. (See R. A. Shepard and P. L. Sciaraffa, J. Org, Chem., 31 (1966) 964). Finally, the oxime is reduced with lithium aluminum hydride in ether, followed by treatment of the ethereal solution with hydrochloric acid to give the amine hydrochloride in 57% yield. (See U.S. Pat. No. 4,378,366).

Attempts to reduce trifluoroacetone oxime catalytically have met with only limited success. The reduction of this oxime over Raney-nickel at 60° C. and at 2000 psi hydrogen pressure in ether is known. (See Ind. Eng. Chem., 48 (1956) 209). Following treatment of the ethereal solution with gaseous HCl, the hydrochloride salt was obtained in 30% yield. Using a similar procedure, except that $PtO_2$ was used as the reduction catalyst, the amine hydrochloride was likewise obtained in 27% yield. (See R. A. Shepard, et al, J, Org, Chem., 31 (1966) 964). Each of these known procedures suffer from drawbacks such as requiring the use of expensive reagents, low yield in one of the reactions, and preparation of the hydrochloride during the isolation procedure, necessitating yet another process step to generate the free amine.

It would therefore be desirable to provide a means to prepare trifluoroisopropylamine by a method more suitable to large-scale manufacture, and which has fewer drawbacks compared to previously known methods. It would be especially desirable to provide a means of reducing trifluoroacetone oxime directly to the amine using a process for which the yield is high and in which the free amine can be isolated without the intermediacy of the hydrochloride salt.

It has now been unexpectedly found that trifluoroisopropylamine can be prepared in good yield and conversion by the catalytic reduction of trifluoroacetone oxime in the vapor phase, with hydrogen in the presence of a reduction catalyst. The results obtained from reducing trifluoroacetone oxime to trifluoroisopropylamine represent a substantial improvement over known methods, catalytic or otherwise. Studies on liquid phase reductions reveal the disadvantageous effect of by-product water on the reaction rate, although the prior art provides no clue of this effect. These studies also show a surprising dependence for trifluoroisopropanol formation on the catalyst. The results of the vapor phase reduction studies were much better. For example, we discovered that the use of platinum, rhodium and/or palladium catalysts, which were not very effective in the liquid phase produce good results in the vapor phase. See examples 9 through 16. It has been discovered that the use of platinum, rhodium and/or palladium catalysts at high temperatures counterbalanced the effect of the byproduct water on the reaction rate. It has been discovered that by conducting the reaction in the vapor phase, the catalyst was able to counteract the effect of the byproduct water on the reaction rate. Compare example 7 with example 12. It was further an unexpected result that the difficulties associated with conversion to the alcohol, due to by-product water, could be overcome with the use of these catalysts at the significantly higher reaction temperatures used in the vapor phase process of this invention.

DESCRIPTION OF THE INVENTION

The invention provides a process for producing trifluoroisopropylamine which comprises reducing trifluoroacetone oxime in the vapor phase with hydrogen in the presence of a reduction catalyst.

The invention also provides a continuous process for producing trifluoroisopropylamine which comprises continuously reducing trifluoroacetone oxime in the vapor phase with gaseous hydrogen in the presence of a reduction catalyst.

In the practice of the present invention, trifluoroacetone oxime is reduced with hydrogen, preferably gaseous hydrogen, in the presence of a reduction catalyst and preferably in the absence of solvents. Trifluoroacetone oxime may be produced by the oximation of trifluoroacetone (R. A. Shepard and P. L. Sciaraffa J. Org. Chem., 31 (1966) 964). The trifluoroacetone oxime is reduced by reacting it with hydrogen. In the preferred embodiment, trifluoroacetone oxime is reacted with at least a stoichiometric amount of hydrogen gas and preferably an excess of hydrogen gas. Preferably the mole ratio of hydrogen to oxime ranges from about 2 to about 50, more preferably from about 2 to about 20, and most preferably from about 2 to about 10.

The reduction of trifluoroacetone oxime takes place in the presence of a reduction catalyst. Suitable reduction catalysts nonexclusively include platinum, rhodium, palladium and combinations thereof These reduction catalysts are commercially available from Engelhard. The reduction catalyst is preferably present on a support, most preferably an inert support. Suitable supports nonexclusively include carbon and alumina. One preferred carbon support is activated carbon of 4–8 mesh. Another preferred alumina support is ⅛" alumina pellets. These supports as well as the catalysts on the supports may be acquired commercially from Engelhard.

In one preferred embodiment, the process of the present invention is conducted where the reduction catalyst comprises platinum, and the support comprises carbon. In another preferred embodiment, the process of the present invention is conducted where the reduction catalyst comprises rhodium, and the support comprises alumina ($Al_2O_3$).

The reduction catalyst is preferably on a support material and present in an amount of from about 0.5% by weight to about 20% by weight, more preferably from about 0.5% by weight to about 15% by weight, and most preferably from about 0.5% by weight to about 10% by weight relative to the support material. Optionally, the catalyst may be pre-treated in order to activate, dry, and remove impurities from the catalyst. Such may be done by heating in an inert gas at a temperature of from about 80° C. to about 300° C. Suitable inert gases for this purpose are nitrogen, helium, argon and combinations thereof. Suitable heating times may easily be determined by those skilled in the art depending on the selection and amount of catalyst. A suitable time is from about 30 minutes to about 90 minutes.

According to the invention, the term "linear hourly space velocity" means the ratio of the volume of gaseous reactants per hour to the volume of the catalyst. For productivity reasons, the reaction is conducted such that the highest linear hourly space velocity that can be attained provided that selectivity and conversion can be maintained at an acceptable level. Typical linear hourly space velocities of the gaseous reactants range from about 100 to about 2000.

The process of the present invention is preferably conducted in the absence of a solvent. The process is preferably conducted at a temperature of from about 80° C. to about 300° C., more preferably from about 100° C. to about 250° C., and most preferably from about 125° C. to about 200° C.

The process may be conducted at a hydrogen pressure of from about 1 to about 50 atmospheres, preferably from about 1 to about 10 atmospheres, and most preferably from about 1 to about 3 atmospheres. Optionally the hydrogen gas may be diluted from about 10% to about 90% with an inert gas such as nitrogen, helium, argon and combinations thereof for better process control.

Optionally the trifluoroisopropylamine is separated and purified, using techniques known in the art, such as by distillation. According the invention, trifluoroisopropylamine can be produced at a purity of at least about 95% as determined by gas chromatography, at a conversion of at least about 90% and at a selectivity of at least about 90%. The conversion and selectivity can be determined by analyzing the composition of the product mixture by gas chromatography. The conversion calculation determines how much of the starting material is now reacted. Selectivity is the ratio of the desired product to total products.

The following non-limiting examples serve to illustrate the invention. It will be appreciated that variations in proportions and alternatives in elements of the components of the composition and processing conditions will be apparent to those skilled in the art and are within the scope of the present invention.

EXAMPLE 1 (COMPARATIVE)

Liquid Phase Reduction:

A 375 ml glass pressure reactor equipped with a magnetic stir bar, pressure gauge, and ball valve was charged with 0.100 g 10% Pd on activated carbon. The reactor was evacuated, and 24.3g trifluoroacetone oxime was added until the pressure was about 36 psi. The liquid portion of the reactor was then placed in an oil bath and heated to 81° C. After 4 hours, the pressure drop of 26 psi indicated that at least 50% of the theoretical hydrogen uptake had occurred. After 7 hours at 80° C., the reaction was stopped and analyzed. GC analysis of the liquid product indicated a 48% conversion of starting material and a selectivity for trifluoroisopropylamine of 69%.

EXAMPLE 2 (COMPARATIVE)

Liquid Phase Reduction:

The same apparatus and procedures were followed as Example 1, except that the reactants included 0.099 g 10% Pd/C, 3.2 g of oxime, and 5 ml diglyme. After 4 hours at 81° C., the pressure drop was zero, indicating no reaction.

EXAMPLE 3 (COMPARATIVE)

Liquid Phase Reduction:

In a manner as described in Example 1, 0.029 g 10% Pd/C, 0.5 g molecular sieves, 2.0 g trifluoroacetone oxime, and 15 ml toluene were heated to 80° C. for 3 days. Analysis of the liquid product indicated 43% conversion of starting material and 70% selectivity for the desired amine.

EXAMPLE 4 (COMPARATIVE)

Liquid Phase Reduction:

In a manner as described in Example 1, 0.025 g 5% $Rh/Al_2O_3$, 0.6 g type 4A molecular sieves, and 2.0 ml trifluoroacetone oxime were heated to 80° C. for 64 hours. The conversion was 75% and the amine selectivity was 68%.

EXAMPLE 5 (COMPARATIVE)

Liquid Phase Reduction:

In a manner as described in Example 5, 0.067 g 5% $Rh/Al_2O_3$ and 4.1 g trifluoroacetone oxime were heated to 89° C. for 3.5 hours. The conversion was 55% and the amine selectivity was 93%.

EXAMPLE 6 (COMPARATIVE)

Liquid Phase Reduction:

In a manner as described in Example 1, 0.057 g 1% Pt/C, 30 ml MeOH and 1 ml conc. HCl and 2.0 g trifluoroacetone oxime were heated to 70° C. for 15 hours. There was no decrease in hydrogen pressure during this time, indicating that no reaction takes place.

EXAMPLE 7 (COMPARATIVE)

Liquid Phase Reduction:

In a manner as described in Example 1, 0.029 g 1% Pt/C and 4.6 g trifluoroacetone oxime were heated to 81° C. for 5 hours. There was no decrease in hydrogen pressure during this time, indicating that no reaction takes place.

EXAMPLE 8 (COMPARATIVE)

Liquid Phase Reduction:

In a manner as described in Example 1, 0.055 g platinum black and 4.6 g trifluoroacetone oxime were heated to 92° C. for 24 hours, followed by 2 hours at 119° C. Analysis indicated a starting material conversion of 79.9%, a selectivity for trifluoroisopropylamine of 27.5% and a selectivity for trifluoroisopropanol of 42.4%.

EXAMPLE 9
Vapor Phase Reduction over 0.5% Rhodium on 1/8" Alumina Pellets at 139° C.

A vertical glass reactor was packed with 20 cc of 0.5% rhodium on 1/8" alumina pellets and pretreated by heating to 150° C. for an hour under a flush of dry nitrogen. The temperature was adjusted to 117° C. under a hydrogen flow of 97 mmol/h. The oxime (96% purity) was metered into the top of the reactor at the rate of 4.2 g/h via a syringe pump. Effluent from the reactor was passed into a trap at room temperature, followed by two −78° C. traps. When the organic flow began, the temperature in the reactor rose and leveled off at 139° C. After a total reaction time of 5 hours, the organic flow was stopped and the reactor was flushed with hydrogen for 1 hour at the reaction temperature. A total of 19.5 g of colorless liquid was collected in the traps. By GC analysis, it consisted of 0% oxime, indicating a 100% starting material conversion and a selectivity for trifluoroisopropylamine of 95.2%. Since the water of reaction (theory 3.0 g), is not seen in this GC analysis, the GC yield of amine is not less than 16.5 g (88% yield). Distillation of 18.3 g of the crude product gave 14.2 g of 98% pure amine, bp 45–47° C., for an isolated yield of 81%.

EXAMPLE 10
Vapor Phase Reduction Over 0.5% Rhodium on 1/8" Alumina Pellets at 147° C.

In a manner and apparatus as described in Example 9, the oxime was passed into the reactor at 5.84 g/h for 2.5 hours, along with hydrogen at 0.144 mol/h at a average temperature of 147° C. The crude product (13.6 g) consisted of 0% oxime, indicating a 100% starting material conversion and a selectivity for trifluoroisopropylamine of 94.0%. Distillation gave 10.4 g of 97% pure trifluoroisopropylamine for a yield of 80%.

EXAMPLE 11
Vapor Phase Reduction Over 0.5% Rhodium on 1/8" Alumina Pellets at 171° C.

In a manner and apparatus as described in Example 9, the oxime was passed into the reactor at 8.25 g/h for 4 hours, along with hydrogen at 0.195 mol/h at a average temperature of 171° C. The crude product (31.7 g ) consisted of 0% oxime, indicating a 100% starting material conversion and a selectivity for trifluoroisopropylamine of 95.3% and 1.5% trifluoroisopropanol. Distillation gave 24.7 g of 99% pure trifluoroisopropylamine for a yield of 84%

EXAMPLE 12
Vapor Phase Reduction Over 0.5% Pt/C at 156° C.

In a manner and apparatus as described in Example 9, the oxime (4.3 g/h) and hydrogen (97 mmol/h) were passed over 20 cc 0.5% Pt on 4–8 mesh activated carbon at an average temperature of 156° C. Analysis of the product mixture indicated a conversion of 100% and a selectivity for trifluoroisopropylamine of 88%. Distillation readily provided the amine in greater than 99% purity.

EXAMPLE 13
Vapor Phase Reduction Over 0.5% Pt/C at 139° C.

In a manner and apparatus as described in Example 12, except that the reaction temperature was 139° C., the oxime was reduced with a conversion of 100% and a selectivity for the amine of 90%. The amine was distilled directly from the product mixture (59% yield).

EXAMPLE 14
Vapor Phase Reduction Over 0.5% Pt/C at 85–156° C.

In a manner and apparatus as described in Example 12, except that the reaction temperature was varied from 85 to 156° C. over the course of two hours. The conversion of oxime was about 75% and the selectivity for the amine was only about 56%. Trifluoroisopropanol was formed in 21% selectivity. It is concluded that both conversion and selectivity are significantly reduced at temperatures below about 125° C.

EXAMPLE 15
Vapor Phase Reduction Over 1% Pd/C at 134° C.

In a manner and apparatus as described in Example 9, the oxime (8.7 g/h) and hydrogen (195 mmol/h) were passed over 20 cc 1% Pd on 4–8 mesh carbon at an average temperature of 134° C. Analysis of the liquid product mixture indicated a starting material conversion of 49.9% and a 76.8% selectivity for the amine. The conversion may be increased by increasing the reaction temperature.

EXAMPLE 16
Vapor Phase Reduction Over 1% Pd/C at 154° C.

In a manner and apparatus as described in Example 13, except that the reaction temperature was 154° C., the organic flow rate was 4.2 g/h, and the hydrogen flow rate was 97 mmol/h, the oxime was reduced with 53.2% conversion and a selectivity for trifluoroisopropylamine of 79.5%. The conversion may be increased by increasing the reaction temperature.

From the foregoing examples it can be seen that an effective process is provided for producing trifluoroisopropylamine by reducing trifluoroacetone oxime with hydrogen the vapor phase in the presence of a reduction catalyst.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A process for producing trifluoroisopropylamine which comprises reducing trifluoroacetone oxime in the vapor phase with hydrogen in the presence of a reduction catalyst.

2. The process of claim 1 wherein the hydrogen has been diluted from about 10% to about 90% with an inert gas.

3. The process of claim 2 wherein the inert gas is selected from the group consisting of nitrogen, helium, argon and combinations thereof.

4. The process of claim 1 further comprising the subsequent step of separating trifluoroisopropylamine.

5. The process of claim 4 wherein said separating step comprises distillation.

6. The process of claim 1, 2, 3, 4 or 5 wherein the trifluoroisopropylamine has a purity of at least about 95%.

7. The process of claim 1 wherein the trifluoroacetone oxime is converted in an amount of at least about 90%.

8. The process of claim 1 wherein trifluoroisopropylamine is produced at a selectivity of at least about 90%.

9. The process of claim 1 which is conducted in the absence of a solvent.

10. The process of claim 1 wherein said process is conducted at a temperature of from about 80° C. to about 300° C.

11. The process of claim 1 wherein said process is conducted at a hydrogen pressure of from about 1 to about 50 atmospheres.

12. The process of claim 1 wherein the mole ratio of hydrogen to oxime ranges from about 2 to about 50.

13. The process of claim 1 wherein the linear hourly space velocity of the gaseous reactants ranges from about 100 to about 2000.

14. The process of claim 1 wherein the reduction catalyst is selected from the group consisting of platinum, rhodium, palladium and combinations thereof.

15. The process of claim 1 wherein the reduction catalyst is activated by heating in an inert gas at a temperature of from about 80° C. to about 300° C.

16. The process of claim 1 wherein the reduction catalyst is present on a support.

17. The process of claim 16 wherein the reduction catalyst is present in an amount of from about 0.5% by weight to about 20% by weight based on the total weight of the catalyst and support.

18. The process of claim 16 wherein the support is selected from the group consisting of carbon and alumina.

19. The process of claim 16 wherein the reduction catalyst comprises platinum and the support comprises carbon.

20. The process of claim 16 wherein the reduction catalyst comprises rhodium and the support comprises alumina.

21. A continuous process for producing trifluoroisopropylamine which comprises continuously reducing trifluoroacetone oxime in the vapor phase with gaseous hydrogen in the presence of a reduction catalyst.

22. The process of claim 21 wherein the reduction catalyst comprises rhodium and the support comprises alumina.

* * * * *